(12) United States Patent
Sawada

(10) Patent No.: US 9,839,796 B2
(45) Date of Patent: Dec. 12, 2017

(54) ULTRASONIC TREATMENT DEVICE AND PROBE

(71) Applicant: OLYMPUS CORPORATION, Hachioji-shi, Tokyo (JP)

(72) Inventor: Yukihiko Sawada, Yoshikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/158,975

(22) Filed: May 19, 2016

(65) Prior Publication Data
US 2016/0263403 A1 Sep. 15, 2016

Related U.S. Application Data

(63) Continuation of application No. PCT/JP2014/079236, filed on Nov. 4, 2014.

(30) Foreign Application Priority Data

Mar. 3, 2014 (JP) ................. 2014-040689

(51) Int. Cl.
*A61B 1/00* (2006.01)
*A61N 7/00* (2006.01)
(Continued)

(52) U.S. Cl.
CPC ........ *A61N 7/00* (2013.01); *A61B 17/320068* (2013.01); *A61B 17/320092* (2013.01);
(Continued)

(58) Field of Classification Search
CPC .............. A61N 7/00; A61B 17/320068; A61B 2017/22015; A61B 17/320092; A61B 17/0047; A61B 17/320076
See application file for complete search history.

(56) References Cited

U.S. PATENT DOCUMENTS 5,695,510 A * 12/1997 Hood ............. A61B 17/320068
30/355
5,906,628 A * 5/1999 Miyawaki ...... A61B 17/320092
606/169

(Continued)

FOREIGN PATENT DOCUMENTS

EP 0 972 493 A2 1/2000
JP 05-003881 B2 1/1993
(Continued)

OTHER PUBLICATIONS

Sep. 6, 2016 International Preliminary Report on Patentability issued in International Patent Application No. PCT/JP2014/079236.
(Continued)

*Primary Examiner* — Richard Louis
(74) *Attorney, Agent, or Firm* — Oliff PLC

(57) ABSTRACT

An ultrasonic treatment device includes a connecting unit. The connecting unit including a first engagement portion which engages with a first screw portion and a second engagement portion which engages with a second screw portion, the connecting unit connecting a probe and a vibration generating unit to transmit the ultrasonic vibrations to the probe by rotation relative to the vibration generating unit and a treatment unit in a first direction around a longitudinal axis, and disconnecting the probe and the vibration generating unit from each other by rotation in a second direction opposite to the first direction.

3 Claims, 11 Drawing Sheets

(51) Int. Cl.
*A61B 17/32* (2006.01)
*A61B 17/00* (2006.01)
*A61B 17/22* (2006.01)

(52) U.S. Cl.
CPC ............... *A61B 2017/00473* (2013.01); *A61B 2017/00477* (2013.01); *A61B 2017/22015* (2013.01); *A61B 2017/320078* (2017.08)

(56) References Cited

U.S. PATENT DOCUMENTS

| | | | |
|---|---|---|---|
| 6,204,592 | B1 | 3/2001 | Hur |
| 2003/0023257 | A1 | 1/2003 | Ishikawa et al. |
| 2008/0269667 | A1* | 10/2008 | Gencarelli ..... A61B 17/320068 604/22 |
| 2008/0294051 | A1 | 11/2008 | Koshigoe et al. |
| 2009/0143796 | A1 | 6/2009 | Stulen et al. |
| 2013/0226041 | A1 | 8/2013 | Akagane |

FOREIGN PATENT DOCUMENTS

| | | |
|---|---|---|
| JP | 10-5238 | 1/1998 |
| JP | 3051999 U | 9/1998 |
| JP | 2005-040222 A | 2/2005 |
| JP | 2008-289876 A | 12/2008 |
| JP | 2011-505194 A | 2/2011 |
| WO | 2012/176735 A1 | 12/2012 |
| WO | 2013/183713 A1 | 12/2013 |

OTHER PUBLICATIONS

Sep. 29, 2015 Japanese Office Action for Japanese Patent Application No. 2015-531186.
Feb. 3, 2015 International Search Report issued in PCT/JP2014/079236.
Sep. 20, 2017 Search Report issued in European Patent Application No. 14884292.5.

* cited by examiner

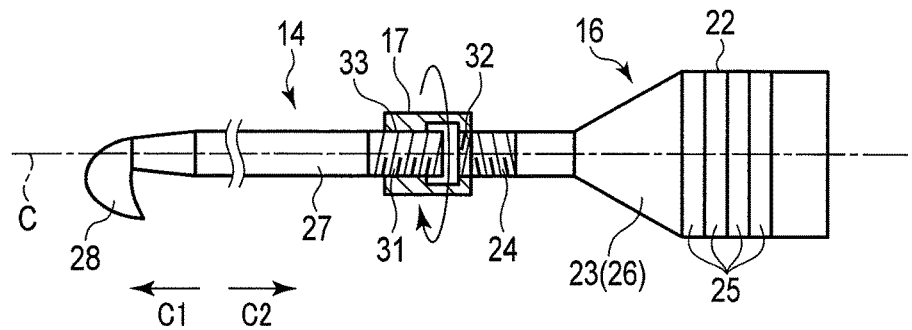
F I G. 5
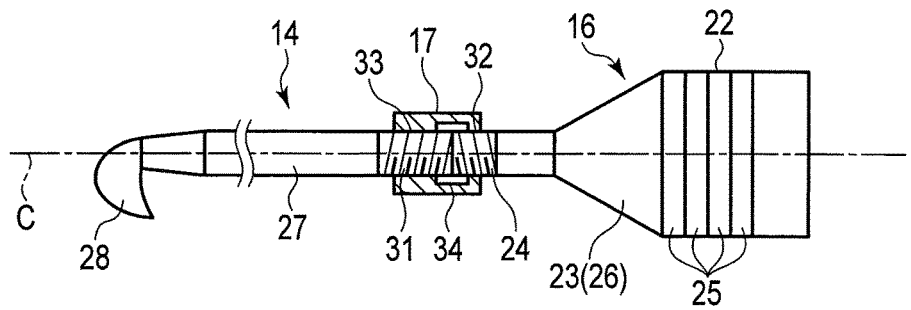
F I G. 6
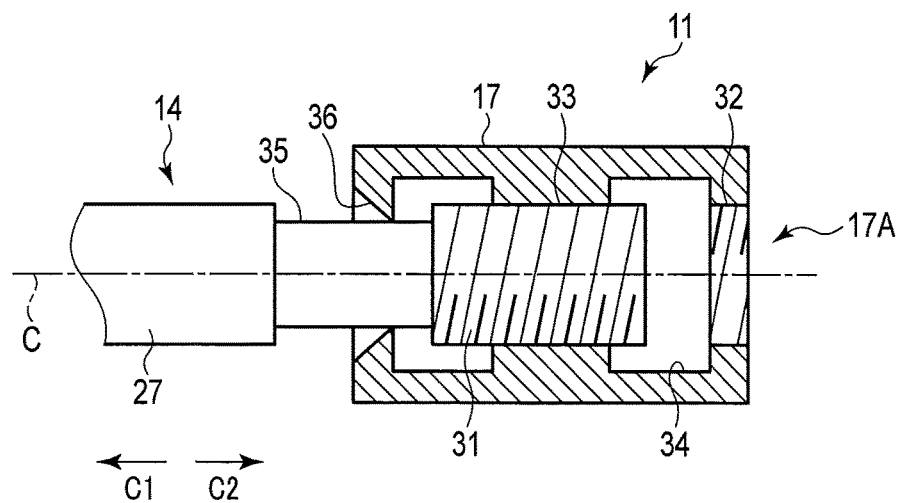
F I G. 7

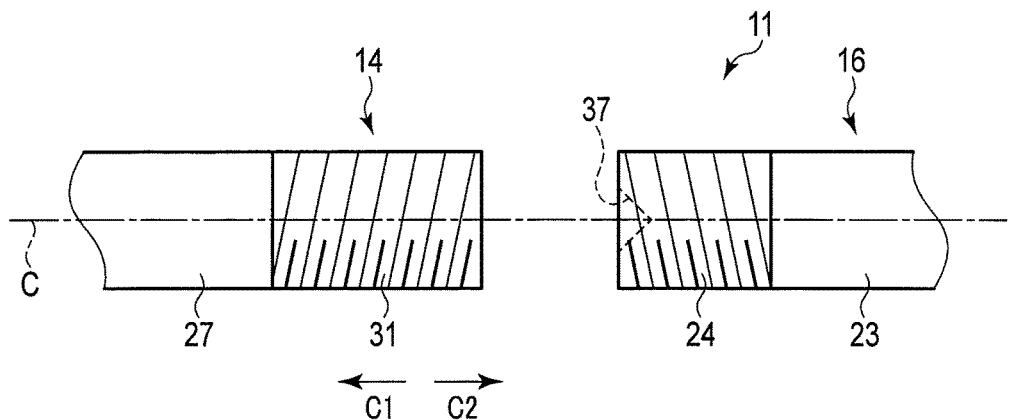
F I G. 8
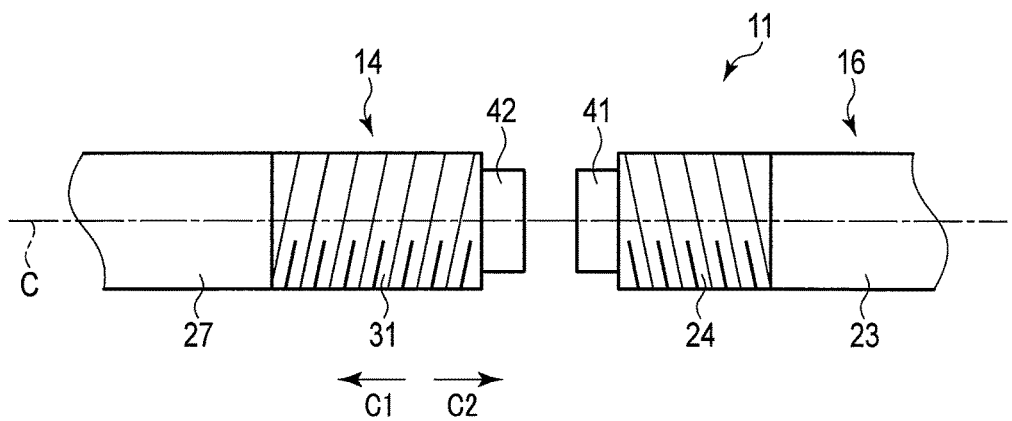
F I G. 9
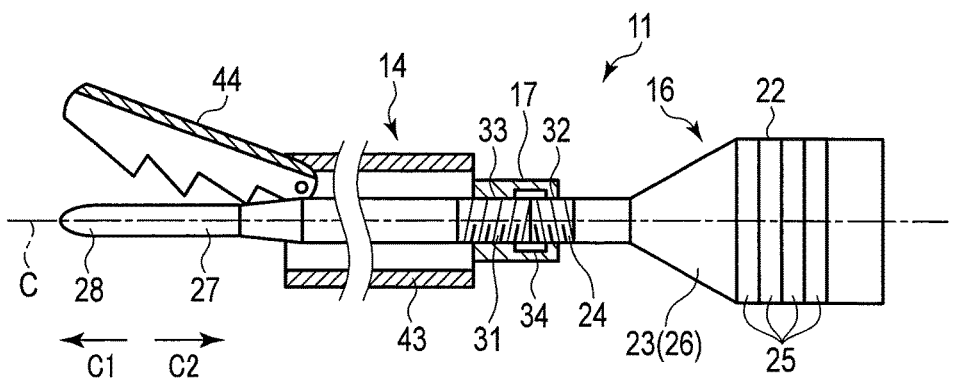
F I G. 10

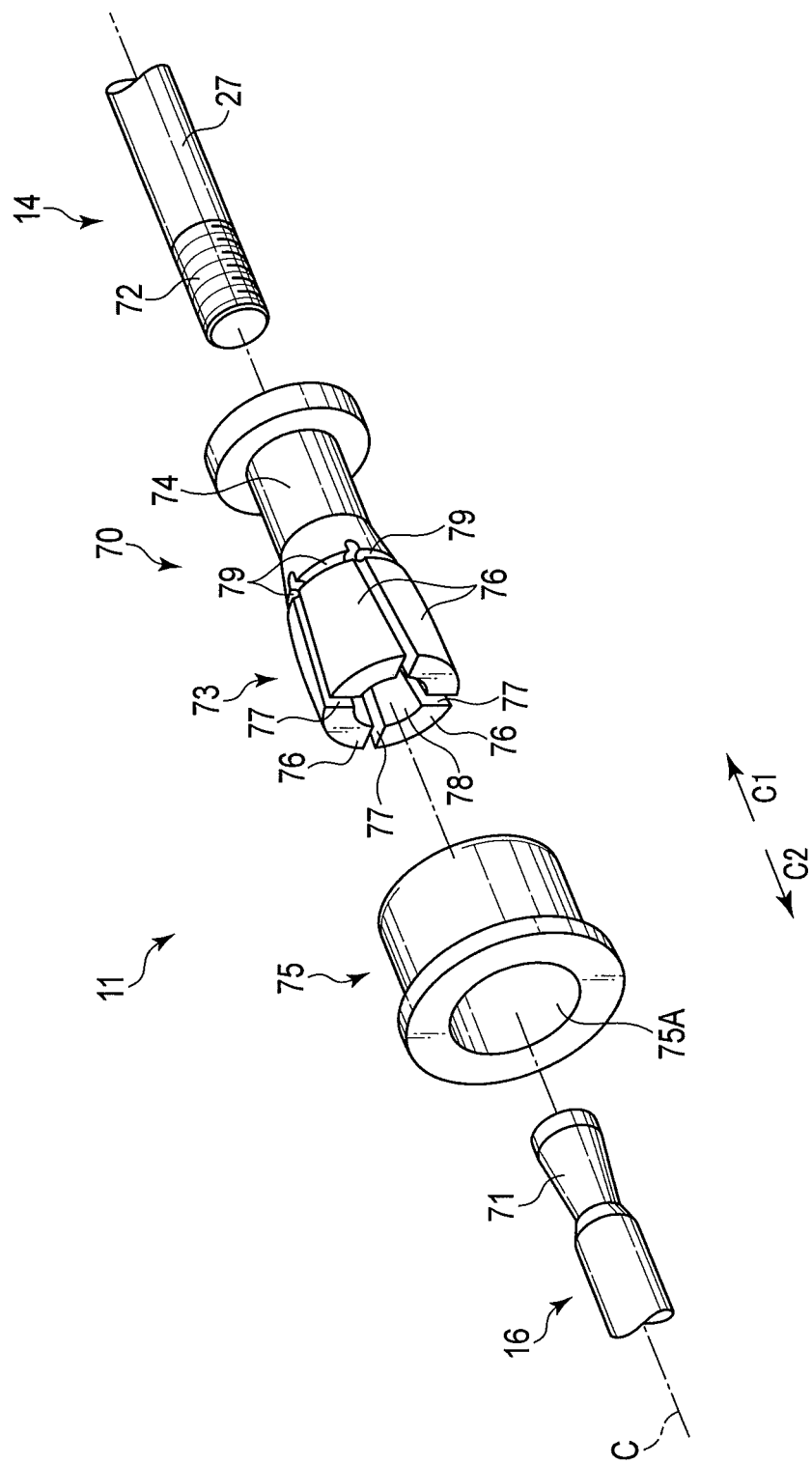
F I G. 20

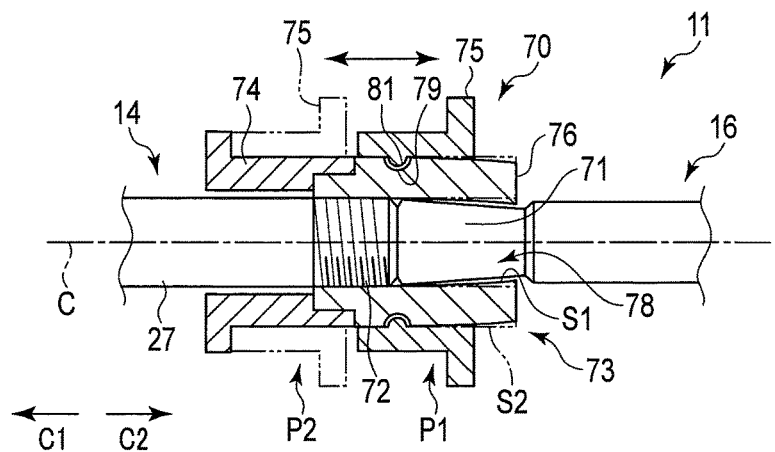
F I G. 21
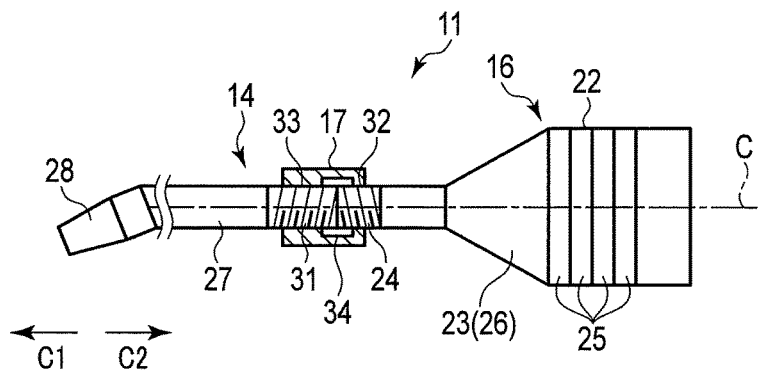
F I G. 22
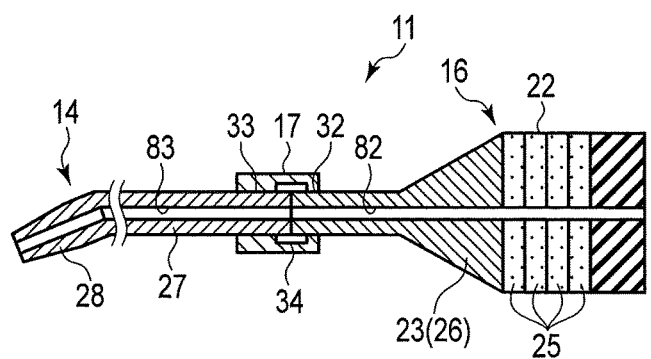
F I G. 23

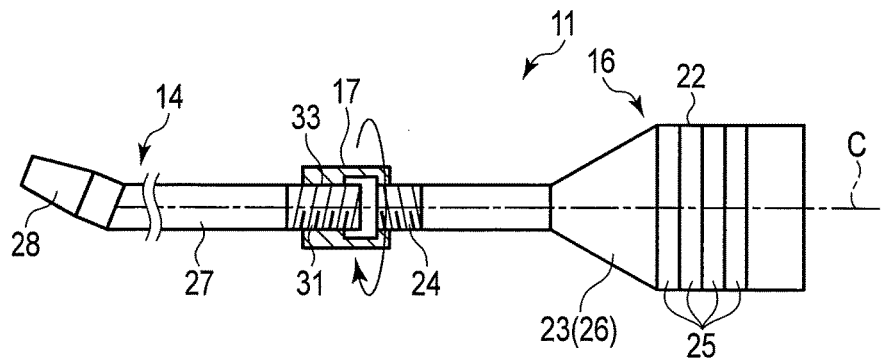
F I G. 24
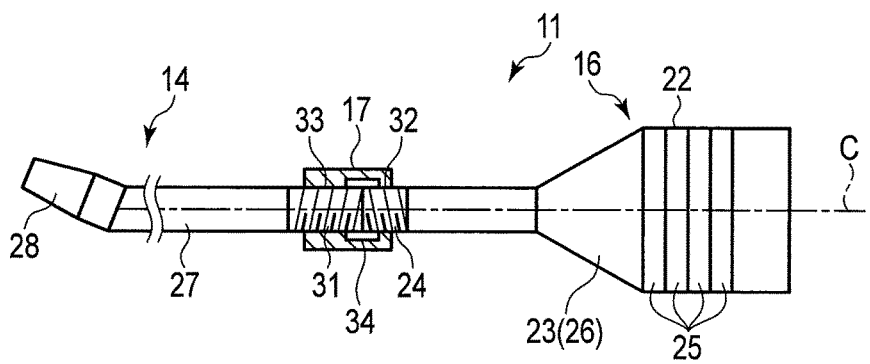
F I G. 25
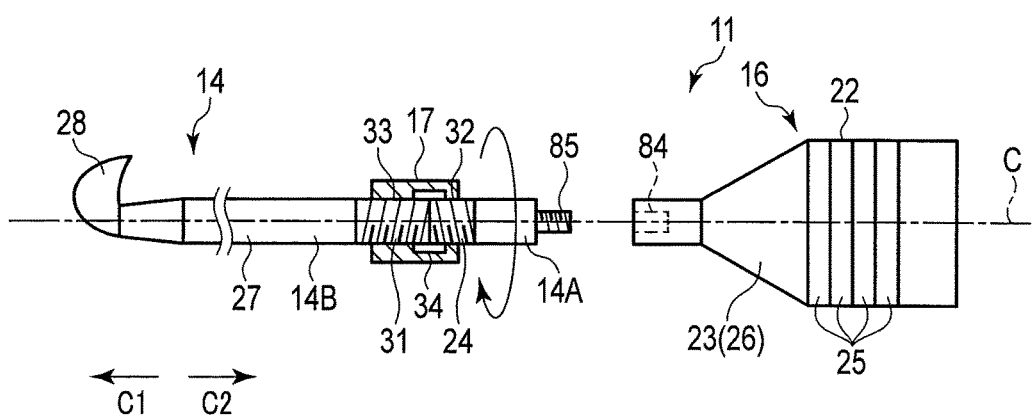
F I G. 26

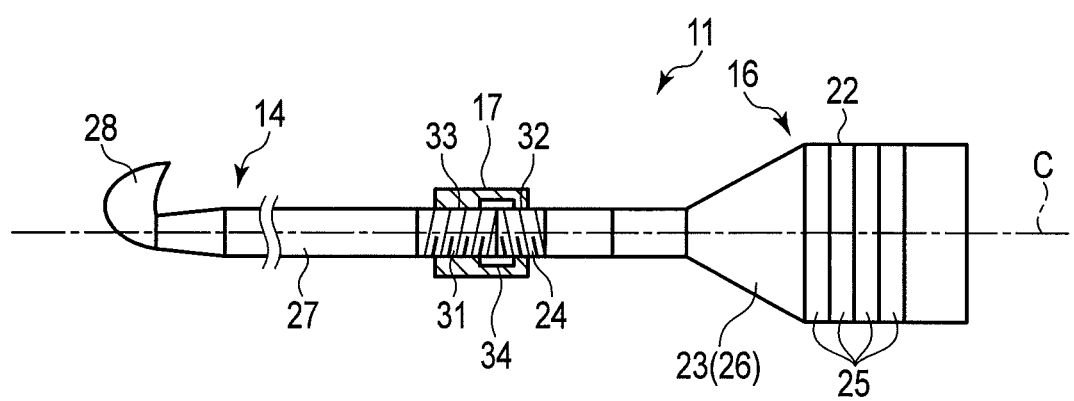
F I G. 27

ULTRASONIC TREATMENT DEVICE AND PROBE

CROSS-REFERENCE TO RELATED APPLICATIONS

This application is a Continuation Application of PCT Application No. PCT/JP2014/079236, filed Nov. 4, 2014 and based upon and claiming the benefit of priority from prior Japanese Patent Application No. 2014-040689, filed Mar. 3, 2014, the entire contents of all of which are incorporated herein by reference.

BACKGROUND OF THE INVENTION

1. Field of the Invention

The present invention relates to an ultrasonic treatment device which treats living tissues by ultrasonic vibrations.

2. Description of the Related Art

Jpn. Pat. Appln. KOKAI Publication No. 10-5238 (Patent Literature 1) discloses a general ultrasonic treatment device. The ultrasonic treatment device comprises a probe. The probe includes a horn, a vibration transmitting rod and a tip piece which treats living tissues. Both ends of the vibration transmitting rod are provided with male screws, which are fixed to female screws respectively provided in the horn and the tip piece.

Jpn. Pat. Appln. KOKAI Publication No. 2005-40222 (Patent Literature 2) also discloses a general ultrasonic treatment device. The ultrasonic treatment device comprises an ultrasonic transmitting member, a horn, and a ring-shaped member which fixes them. A convex portion of the horn is fit in a concave portion of the ultrasonic transmitting member, and the ring-shaped member is screwed with a male screw portion of the ultrasonic transmitting member. As a result, the ultrasonic transmitting member is prevented from rotating around an axis.

CITATION LIST

Patent Literature

Patent Literature 1: Jpn. Pat. Appln. KOKAI Publication No. 10-5238

Patent Literature 2: Jpn. Pat. Appln. KOKAI Publication No. 2005-40222

BRIEF SUMMARY OF THE INVENTION

Various ultrasonic treatment devices are used depending on the living tissues to be treated. The ways of using an ultrasonic treatment device vary from doctor to doctor. Thus, there is a need for an ultrasonic treatment device that can be flexibly applied to various treatments.

An object of the present invention is to provide an ultrasonic treatment device with great versatility.

Solution to Problem

An ultrasonic treatment device comprises; a vibration generating unit which includes a first screw portion and generates ultrasonic vibrations; a probe including a probe main body which extends along a longitudinal axis and to which the ultrasonic vibrations generated by the vibration generating unit are transmitted, a second screw portion which is provided at the probe main body to face the first screw portion and has a spiral in an opposite direction to that of the first screw portion, and a treatment unit provided at a distal end portion of the probe main body; and a connecting unit including a first engagement portion which engages with the first screw portion and a second engagement portion which engages with the second screw portion, the connecting unit connecting the probe and the vibration generating unit to transmit the ultrasonic vibrations to the probe by rotation relative to the vibration generating unit and the treatment unit in a first direction around the longitudinal axis, and disconnecting the probe and the vibration generating unit from each other by rotation in a second direction opposite to the first direction.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 5 is a side view showing a step of fastening the connecting unit of the ultrasonic treatment device shown in FIG. 4 to a first engagement portion of the vibration generating unit.

FIG. 6 is a side view showing a state in which the probe is fixed to the vibration generating unit, where the position of the treatment unit shown in FIG. 5 has been changed.

FIG. 7 is a sectional view showing a first modification of the ultrasonic treatment device of the first embodiment.

FIG. 8 is a schematic view showing a second modification of the ultrasonic treatment device of the first embodiment.

FIG. 9 is a schematic view showing a third modification of the ultrasonic treatment device of the first embodiment.

FIG. 10 is a partly cutaway schematic view of a fourth modification of the ultrasonic treatment device of the first embodiment.

FIG. 20 is a side view showing a vibration generating unit, a probe and a chuck of the ultrasonic treatment device of a third embodiment.

FIG. 21 is a sectional view showing a portion around the chuck of the ultrasonic treatment device shown in FIG. 20, taken along a plane passing through a longitudinal axis.

FIG. 22 is a partly cutaway side view showing a vibration generating unit, a probe and a chuck of the ultrasonic treatment device of a fourth embodiment.

FIG. 23 is a sectional view showing the vibration generating unit, the probe and the connecting unit shown in FIG. 22, taken along a plane including the longitudinal axis.

FIG. 24 is a side view showing a step of fastening the connecting unit to a first engagement portion and a second engagement portion, where the position of the treatment unit of the ultrasonic treatment device shown in FIG. 22 has been changed.

FIG. 25 is a side view showing a state in which the connecting unit of the ultrasonic treatment device shown in FIG. 24 is fastened to the first engagement portion and a second engagement portion.

FIG. 26 is a side view showing a state in which a second connecting end of the ultrasonic treatment device of a fifth embodiment is removed from a first connecting end.

FIG. 27 is a side view showing a state in which the second connecting end is fixed to the first connecting end of the ultrasonic treatment device shown in FIG. 26.

DESCRIPTION OF EMBODIMENTS

First Embodiment

The first embodiment of the present invention will be explained with reference to FIG. 1 to FIG. 6.

An ultrasonic treatment device 11 comprises a hand piece 12 and a power supply unit 13. The ultrasonic treatment device 11 has a longitudinal axis C. One of two directions parallel to the longitudinal axis C is referred to as a distal direction C1 (see FIG. 1) and a direction opposite to the distal direction is referred to as a proximal direction C2 (see FIG. 1). The longitudinal axis C coincides with a longitudinal axis C of a probe 14 to be described later.

Figure 1:
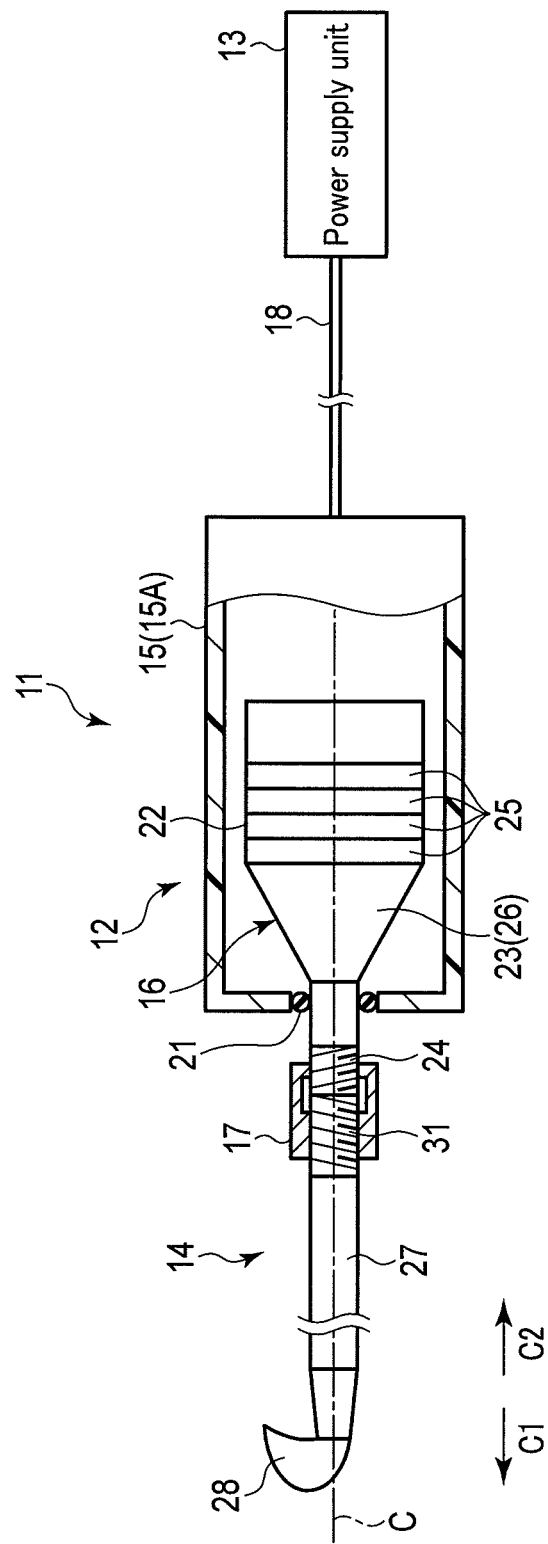
FIG. 1 is a partly cutaway schematic view of an ultrasonic treatment device of a first embodiment, showing an inner part of the ultrasonic treatment device.

As shown in FIG. 1, the hand piece 12 comprises a grip 15 constituting an outer shell, a vibration generating unit 16 housed in the grip 15, a probe 14 connected to the vibration generating unit 16, and a connecting unit 17 connecting the vibration generating unit 16 and the probe 14. The grip 15 is connected to one end of a cable 18. The other end of the cable 18 is connected to the power supply unit 13.

As shown in FIG. 1, the grip 15 includes a cylindrical holder case 15A. A doctor who is a user can use the ultrasonic treatment device 11 by holding the holder case 15A. The vibration generating unit 16 is housed inside the holder case 15A. Waterproofing packing 21 is provided between the holder case 15A and the probe 14. An energy operation input button is mounted on the holder case 15A. The doctor can apply ultrasonic vibrations to living tissues of a subject of treatment by operating the energy operation input button. A cushioning material (elastic material) to absorb vibrations generated from the vibration generating unit 16 may be provided between the inner surface of the holder case 15A and the vibration generating unit 16.

Figure 3:
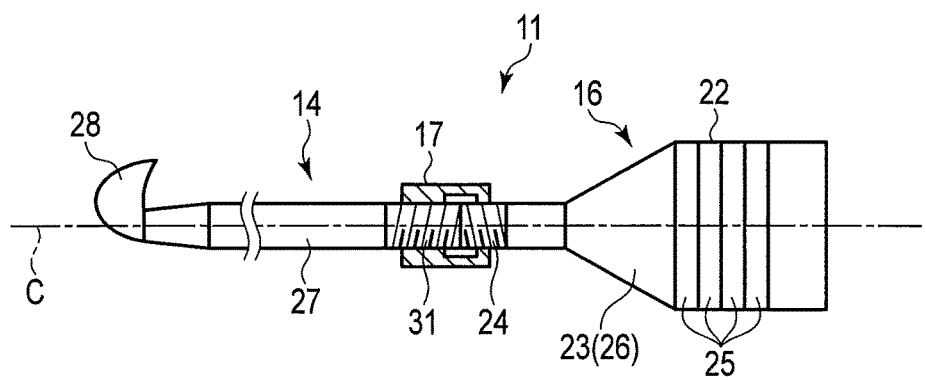
FIG. 3 is a partly cutaway side view showing a vibration generating unit, a probe and a connecting unit of the ultrasonic treatment device shown in FIG. 1.

As shown in FIG. 1 and FIG. 3, the vibration generating unit 16 comprises an ultrasonic vibrator 22, a horn member 23 and a first screw portion 24. The ultrasonic vibrator 22 comprises piezoelectric elements 25 (four elements in this embodiment), which change an electric current to ultrasonic vibrations. The ultrasonic vibrator 22 is connected to one end of an electrical wiring. The electrical wiring extends inside the cable 18 and connects with the power supply unit 13 at the other end. Power is supplied from the power supply unit 13 to the ultrasonic vibrator 22 through the electrical wiring, with the result that ultrasonic vibrations occur at the ultrasonic vibrator 22.

The ultrasonic vibrator 22 is attached to the horn member 23. The horn member 23 is formed of a metal material. The horn member 23 has a cross-section change portion 26, whose cross section perpendicular to the longitudinal axis C is reduced toward the distal direction C1. The ultrasonic vibrations generated by the ultrasonic vibrator 22 are transmitted to the horn member 23. Amplitudes of the ultrasonic vibrations are increased by the cross-section change portion 26.

The first screw portion 24 is provided on a distal end of the horn member 23. In this embodiment, the first screw portion 24 comprises a male screw, more specifically, a right-handed screw (which moves forward to an inner portion by a clockwise rotation).

The probe 14 is formed of, for example, a biocompatible metal material (e.g., a titanium alloy). As shown in FIG. 3, the probe 14 comprises a probe main body 27 extended along the longitudinal axis C, a second screw portion 31 provided on the probe main body 27 to face the first screw portion 24, and a treatment unit 28 provided on the side of the distal direction side of the probe main body 27.

The probe main body 27 has a rod shape extending along the longitudinal axis C. The treatment unit 28 has, for example, a blade extending in a direction crossing the longitudinal axis C; that is, it has a hook-like shape. The second screw portion 31 is provided on a proximal end side of the probe main body 27. The second screw portion 31 comprises a male screw, more specifically, a left-handed screw (which moves forward to an inner portion by a counterclockwise rotation). Thus, the second screw portion 31 has a spiral in an opposite direction to that of the first screw portion 24.

Figure 2:
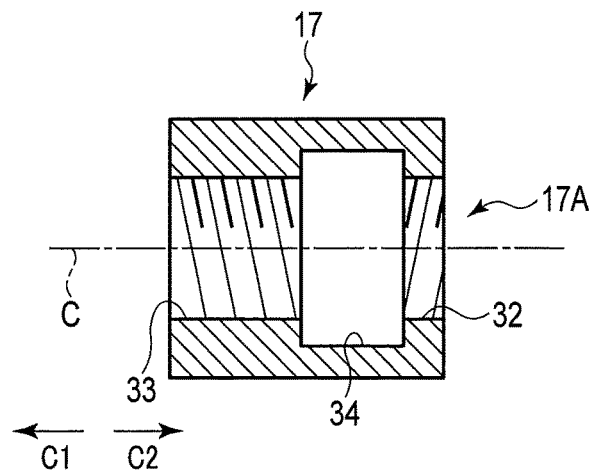
FIG. 2 is a sectional view showing a connecting unit of the ultrasonic treatment device shown in FIG. 1.

As shown in FIG. 2, the connecting unit 17 has a ring shape (cylindrical shape) and is formed of, for example, a material for a normal mechanical structure (e.g., a titanium alloy, an aluminum alloy, steel, metallic glass, resin, or fiber-reinforced resin). The connecting unit 17 has a through hole 17A in the center, extending along the longitudinal axis. The connecting unit 17 has, along the through hole 17A, a first engagement portion 32 which is engaged with the first screw portion 24, a second engagement portion 33 which is engaged with the second screw portion 31, and a hollow clearance portion 34 located between the first engagement portion 32 and the second engagement portion 33. The connecting unit 17 is provided at a position apart from a node of ultrasonic vibrations (for example, provided at or near an antinode of ultrasonic vibrations).

The first engagement portion 32 comprises a female screw corresponding to the first screw portion 24, which is a right-handed screw. The second engagement portion 33 comprises a female screw corresponding to the second screw portion 31, which is a left-handed screw. Thus, the second engagement portion 33 has a spiral in an opposite direction to that of the first engagement portion 32. The connecting unit 17 is configured to connect the vibration generating unit 16 and the probe 14, in a state where the first screw portion 24 on the side of the vibration generating unit 16 butts against the second screw portion 31 on the side of the probe 14.

The ultrasonic vibrations generated by the ultrasonic vibrator 22 are transmitted to the probe main body 27 of the probe 14 through the horn member 23. In the connecting unit 17, since the first screw portion 24 and the second screw portion 31 butt against each other at constant pressure, the ultrasonic vibrations on the side of the vibration generating unit 16 are smoothly transmitted to the side of the probe 14. The ultrasonic vibrations are transmitted to the treatment unit 28 through the probe main body 27, and are able to treat a subject of treatment (living tissue) in the treatment unit 28.

Functions of the ultrasonic treatment device 11 of the embodiment will be described with reference to FIG. 3 to FIG. 6. In the state where the ultrasonic treatment device 11 of the embodiment has been assembled, a tip of the treatment unit 28 projects toward the upper side of the figure, for example, as shown in FIG. 3.

Figure 4:
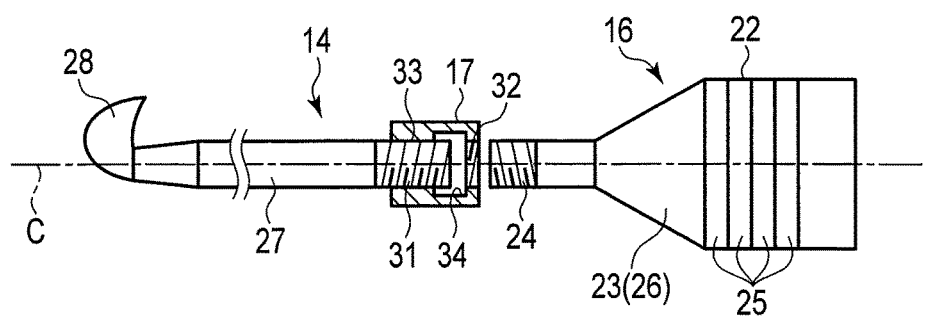
FIG. 4 is a side view showing a state in which the probe and the connecting unit of the ultrasonic treatment device shown in FIG. 3 are removed from the vibration generating unit.

When performing surgery, to change the position of the tip of the treatment unit 28, the doctor rotates the probe 14 and the connecting unit 17 clockwise (in a second direction) as viewed from the proximal direction C2 around the longitudinal axis C, thereby releasing the engagement between the first screw portion 24 and the first engagement portion 32, as shown in FIG. 4. Then, as shown in FIG. 5, the treatment unit 28 is arranged at a desired position (for example, the position where the tip of the treatment unit 28 projects toward the bottom side of the figure) and the connecting unit 17 is made to face to the first screw portion 24. In this state, the probe 14 is held by one hand (for example, the left hand) to maintain the angle of the probe 14. At the same time, while a portion near a distal end of the vibration generating unit 16 is supported by the ring finger and the little finger of the other hand (for example, the right hand), the connecting unit 17 is rotated counterclockwise (in a first direction) as viewed from the proximal direction C2 around the longitudinal axis C with the thumb and the index finger of the other hand. As a result, the second screw portion 31 on the side of the probe 14 is pulled in toward an inner part of the connecting unit 17 (toward the clearance portion 34). At the same time, the first screw portion 24 on the side of the vibration generating unit 16 is also pulled in toward an inner part of the connecting unit 17 (toward the clearance portion 34). When the connecting unit 17 is rotated by a predetermined angle, the end face of the first screw portion 24 is made to butt against the end face of the second screw portion 31. When the end face of the first screw portion 24 butts against the end face of the second screw portion 31 and a predetermined pressure is applied, as shown in FIG. 6, ultrasonic vibrations can be transmitted from the vibration generating unit 16 to the side of the probe 14. Thus, the doctor can easily change the angle (position) of the treatment unit 28. After changing the angle of the treatment unit 28, the doctor can promptly restart the treatment.

The length of the probe 14 and the vibration generating unit 16 (the horn member 23) along the longitudinal axis C, which most influences the drive frequency (resonance frequency of the ultrasonic vibrations), has a constant value, since the end face of the first screw portion 24 butts against the end face of the second screw portion 31.

According to the first embodiment, the ultrasonic treatment device 11 comprises: the vibration generating unit 16 which includes the first screw portion 24 and generates ultrasonic vibrations; the probe 14 including the probe main body 27 which extends along the longitudinal axis C and to which the ultrasonic vibrations generated by the vibration generating unit 16 are transmitted, the second screw portion 31 which is provided at the probe main body 27 to face the first screw portion 24 and has a spiral in an opposite direction to that of the first screw portion 24, and the treatment unit 28 provided at a distal end portion of the probe main body 27; and the connecting unit 17 including the first engagement portion 32 which engages with the first screw portion 24 and the second engagement portion 33 which engages with the second screw portion 31, wherein the connecting unit 17 connects the probe 14 and the vibration generating unit 16 so as to transmit ultrasonic vibrations to the side of the probe 14 by rotation relative to the vibration generating unit 16 and the treatment unit 28 in the first direction around the longitudinal axis C, and disconnects the probe 14 and the vibration generating unit 16 from each other by rotation in the second direction opposite to the first direction.

The configuration described above realizes the ultrasonic treatment device 11 with a simple structure, in which an angular position of the probe 14 (the treatment unit 28) about the axis can be freely changed. Accordingly, when performing manipulations, the operator can easily access an operative field with an increased degree of freedom. Therefore, the reliability and safety of operations can be improved and fatigue of the operator can be reduced. Further, since the connecting unit 17 connects the probe 14 and the vibration generating unit 16 so as to transmit ultrasonic vibrations to the side of the probe 14, loss of ultrasonic vibrations at a boundary position between the vibration generating unit 16 and the probe 14 can be suppressed to a minimum.

The connecting unit 17 is provided at a position apart from a node of ultrasonic vibrations. With the above configuration, loss of ultrasonic vibrations at a connecting portion between the vibration generating unit 16 and the probe 14 can be suppressed to a minimum. Since stress is the greatest at the nodes, vibration energy is easily lost at the nodes.

Each of the first screw portion 24 and the second screw portion 31 is formed of a male screw, and each of the first engagement portion 32 and the second engagement portion 33 is formed of a female screw. The configuration described above realizes the ultrasonic treatment device 11 with a very simple structure, in which an angle of the probe 14 can be freely changed.

If the probe 14 is a single-use product, at least a part of the connecting unit 17 may be formed of a material which is not resistant to sterilization, such as autoclaving (for example, a resin material having a low fusing or softening point). In this case, unintended reuse of the probe 14 can be prevented.

A first modification of the ultrasonic treatment device 11, in which a part of the connecting unit 17 is modified, will be described with reference to FIG. 7. In the modification, parts of the connecting unit 17 and the probe 14 are different in shape from those of the first embodiment. The other parts are the same as those of the first embodiment.

In the modification, a recess 35 is provided in a part of the probe main body 27 on the side of the proximal direction C2. The recess 35 is provided in a position adjacent to the second screw portion 31. The recess 35 is provided as an annular concave portion recessed from the outer circumference of the probe main body 27.

The connecting unit 17 has a fitting portion 36 projecting toward the center. The connecting unit 17 has a cylindrical shape, which may be formed by joining, for example, two arc-like members (members having semicircular cross sections) with brazing or the like. The fitting portion 36 is fit in the recess 35 and prevents the connecting unit 17 from detaching from the probe 14.

In this modification, the connecting unit 17 does not detach from the probe 14. Thus, when the doctor changes an angular position of the probe 14 about the axis during an operation, a risk of the connecting unit 17 detaching and being lost can be prevented. The recess 35 of the modification may be provided near the first screw portion 24 of the vibration generating unit 16, so that the connecting unit 17 may not detach from the vibration generating unit 16. However, ordinarily, the probe 14 is a so-called single-use product that can be used only once, whereas the vibration generating unit 16 is designed to be reprocessed and repeatedly used. Therefore, the connecting unit 17 on the side of probe 14 should preferably have an annular structure. With this modification, when the vibration generating unit 16 is reprocessed, the operator's burden can be reduced and the structure which has little likelihood of reprocess defect is achieved.

A second modification of the ultrasonic treatment device 11, in which a part of the first screw portion 24 is modified, will be described with reference to FIG. 8. In this modification, a part of the first screw portion 24 is different in shape from that of the first embodiment; the other parts are the same as those of the first embodiment.

The first screw portion 24 has in a central portion of its end face a concave portion 37, which is, for example, cone-shaped. The concave portion 37 is not limited to a cone shape, but may be of another shape, such as a hemisphere or a cylindrical shape. According to the modification, a projection, which may be frequently seen in a section cut by a lathe, can be relieved by the concave portion 37. With this configuration, the second screw portion 31 can securely butt against the first screw portion 24 while a pressure is applied. Therefore, transmission loss of ultrasonic vibrations between the vibration generating unit 16 and the probe 14 can be reduced. The concave portion 37 is provided in the first screw portion 24 in this modification. However, the concave portion 37 may be provided in a central portion of the end face of the second screw portion 31, or the concave portion 37 may be provided in a central portion of the end face of each of the first screw portion 24 and the second screw portion 31. In other words, the concave portion 37 may be provided in a central portion of at least one of the end face of the first screw portion 24 and the end face of the second screw portion 31.

A third modification of the ultrasonic treatment device 11, in which parts of the first screw portion 24 and the second screw portion 31 are modified, will be described with reference to FIG. 9. In this modification, parts of the first screw portion 24 and the second screw portion 31 are different in shape from those of the first embodiment; the other parts are the same as those of the first embodiment.

The first screw portion 24 has a first projection 41, which is cylindrical and projects toward the side of the second screw portion 31 (the side of the probe 14). The second screw portion 31 has a second projection 42, which is cylindrical and projecting toward the side of the first screw portion 24 (the side of the vibration generating unit 16). In a state where the probe 14 and the vibration generating unit 16 are connected, the end face of the first projection 41 is made to butt against the end face of the second projection 42 in the clearance portion 34. In this modification, even in a position apart from the clearance portion 34, the first screw portion 24 and the second screw portion 31 can butt against each other. For example, even in a state where the first screw portion 24 is located in a middle portion of the first engagement portion 32, the first screw portion 24 can butt against the second screw portion 31 at a position overlapping the first engagement portion 32. Thus, in this modification, the dimensions of the clearance portion 34 need not be strictly controlled; that is, the strictness of the dimension tolerance of the clearance portion 34 can be relaxed. Both the first projection 41 and the second projection 42 may not necessarily be provided, but at least one of them may be provided.

A fourth modification of the ultrasonic treatment device 11, in which the structure of a peripheral portion attached to the probe 14 is modified, will be described with reference to FIG. 10. This modification differs from the first embodiment in that it comprises a cylindrical probe 14 and a grasping member 44 for grasping living tissue in association with the probe 14; the other parts are the same as those of the first embodiment.

In this modification, the probe 14 comprises a treatment unit 28, which is, for example, rod-shaped. A hand piece 12 comprises a sheath 32 encircling the probe 14, and a grasping member 44 rotatably attached to a distal end portion of the sheath 43 by a pin. The grasping member 44 is rotatable between a position in engagement with the probe 14 and a position separated from the probe 14.

In this modification, to change the position of the grasping member 44, the doctor rotates the probe 14, the sheath 43, and the connecting unit 17 clockwise as viewed from the proximal direction C2 around the longitudinal axis C, thereby releasing the engagement between the first screw portion 24 and the first engagement portion 32. Then, the grasping member 44 is arranged in a desired position, and the sheath 43 is held by one hand (for example, the left hand) to maintain the angle of the grasping member 44. At the same time, while a portion near the distal end of the vibration generating unit 16 is supported by the ring finger and the little finger of the other hand (for example, the right hand), the connecting unit 17 is rotated counterclockwise as viewed from the proximal direction C2 around the longitudinal axis C with the thumb and the index finger of the other hand. As a result, the end face of the first screw portion 24 butts against the end face of the second screw portion 31, and the vibration generating unit 16 and the probe 14 are connected so that ultrasonic vibrations can be transmitted from the vibration generating unit 16 to the side of the probe 14. Thus, the doctor can easily change the angle (position) of the treatment unit 28 and the grasping member 44 about the axis. After changing the angle of the treatment unit 28, the doctor can restart the treatment promptly.

Second Embodiment

An ultrasonic treatment device 11 of a second embodiment will be described with reference to FIG. 11 to FIG. 14.

The ultrasonic treatment device 11 of the second embodiment differs from the first embodiment in the shapes of the first screw portion 24, the second screw portion 31, the first engagement portion 32 and the second engagement portion 33; the other parts are the same as those of the first embodiment, therefore, mainly portions different from the first embodiment will be explained. Portions that are the same as the first embodiment will not be explained or illustrated in the drawings.

Figure 11:
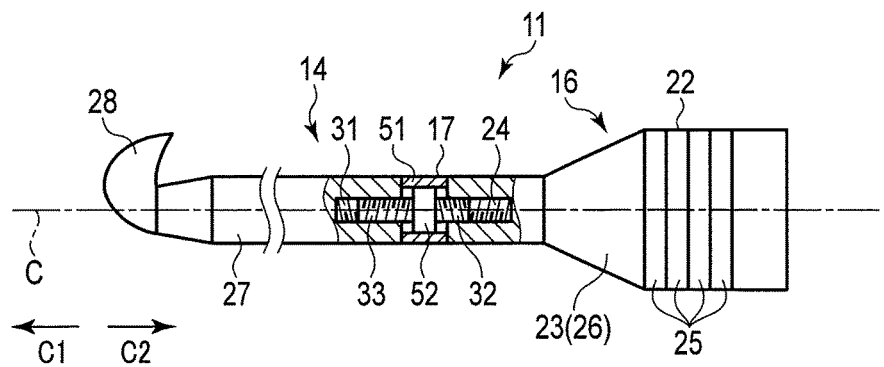
FIG. 11 is a partly cutaway side view showing a vibration generating unit, a probe and a connecting unit of the ultrasonic treatment device of the second embodiment.

As shown in FIG. 11, a vibration generating unit 16 comprises an ultrasonic vibrator 22, a horn member 23 and a first screw portion 24. The ultrasonic vibrator 22 and the horn member 23 are in the same configuration as those of the first embodiment.

The first screw portion 24 is provided on a distal end of the horn member 23. In this embodiment, the first screw portion 24 comprises a female screw, more specifically, a female screw corresponding to the first engagement portion 32 comprising a right-handed screw.

The probe 14 comprises a probe main body 27 extended along the longitudinal axis C, a second screw portion 31 provided on the probe main body 27 to face the first screw portion 24, and a treatment unit 28 provided on the side of the distal direction C1 of the probe main body 27. The probe main body 27 and the treatment unit 28 are the same in configuration as those of the first embodiment.

The second screw portion 31 comprises a female screw, more specifically, a female screw corresponding to the second engagement portion 33 comprising a left-handed screw. Thus, the second screw portion 31 has a spiral in an opposite direction to that of the first screw portion 24.

Figure 12:
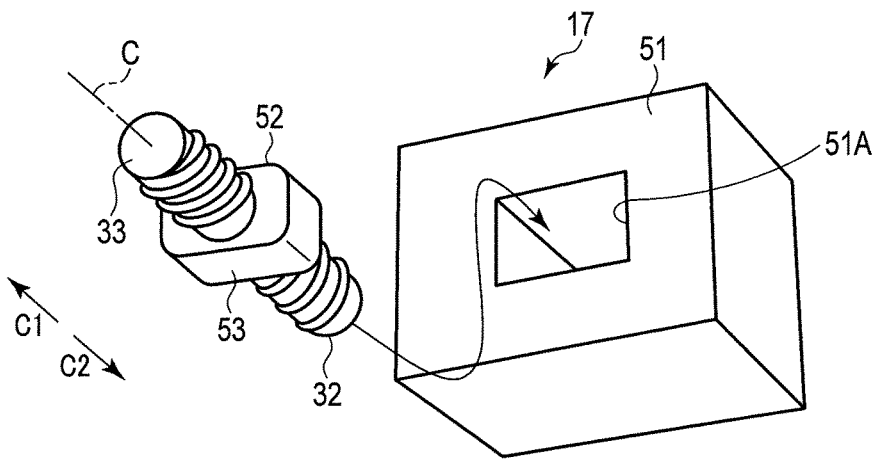
FIG. 12 is a perspective view showing a spacing member and a fastening member of the connecting unit shown in FIG. 11.

As shown in FIG. 11 and FIG. 12, a connecting unit 17 comprises an annular spacing member 51, and a fastening member 52 inserted through the spacing member 51. Each of the spacing member 51 and the fastening member 52 has a ring shape (cylindrical shape) and is formed of, for example, a metal material for a mechanical structure, which preferably lightly damps ultrasonic waves (e.g., a titanium alloy, an aluminum alloy, steel or metallic glass). The spacing member 51 is quadrangular or oval. The spacing member 51 includes a quadrangular through hole 51A extending through the spacing member 51 in the direction of the longitudinal axis C. The spacing member 51 can be rotated by a finger, a spanner, etc. The connecting unit 17 is provided at a position apart from a node of ultrasonic vibrations (for example, provided at or near an antinode of ultrasonic vibrations).

As shown in FIG. 12, the fastening member 52 includes a fastening member main body 53, a first engagement portion 32 projecting from the fastening member main body 53 toward a side of the proximal direction C2 along the longitudinal axis C, and a second engagement portion 33 projecting from the fastening member main body 53 toward a side of the distal direction C1 along the longitudinal axis C. The fastening member main body 53 is shaped as a substantially square pole, and four edges along the longitudinal axis C are chamfered. The first engagement portion 32 comprises a male screw, more specifically, a right-handed screw. The second engagement portion 33 comprises a male screw, more specifically, a left-handed screw. Thus, the second engagement portion 33 has a spiral in an opposite direction to that of the first engagement portion 32.

The fastening member main body 53 is configured to closely fit within the through hole 51A of the spacing member 51. The fastening member 52 is fit within the through hole 51A to be movable relative to the spacing member 51 in the direction along the longitudinal axis C.

The fastening member 52 is rotatable around the longitudinal axis C together with the spacing member 51.

As shown in FIG. 11, the connecting unit 17 is configured to connect the vibration generating unit 16 and the probe 14 in a state where a predetermined pressure is applied to the spacing member 51 sandwiched between the vibration generating unit 16 and the probe 14. Thus, the connecting unit 17 is configured to connect the probe 14 and the vibration generating unit 16 so as to transmit ultrasonic vibrations to the side of the probe 14.

The ultrasonic vibrations generated by the ultrasonic vibrator 22 are transmitted to the probe main body 27 of the probe 14 through the horn member 23. In the connecting unit 17, since the vibration generating unit 16 and the probe 14 are fixed with the spacing member 51 sandwiched therebetween, the ultrasonic vibrations are smoothly transmitted from the side of the vibration generating unit 16 to the side of the probe 14. The ultrasonic vibrations are transmitted to the treatment unit 28 through the probe main body 27, and are able to treat a subject of treatment (living tissue) in the treatment unit 28.

Figure 13:
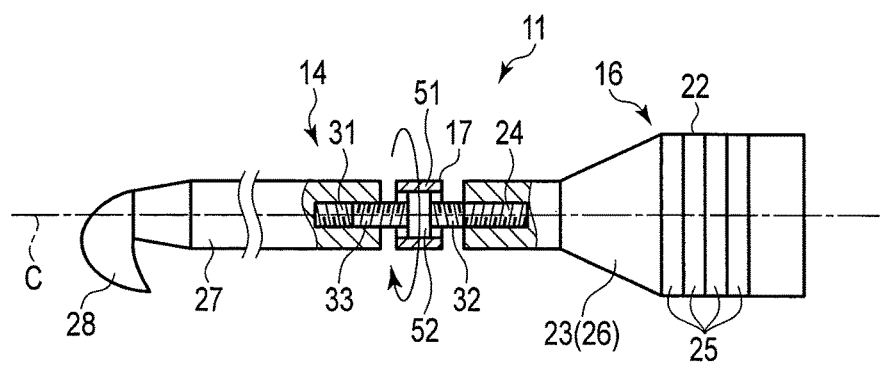
FIG. 13 is a side view showing a step of fastening the connecting unit to a first engagement portion and a second engagement portion, where the position of the treatment unit of the ultrasonic treatment device shown in FIG. 11 has been changed.
Figure 14:
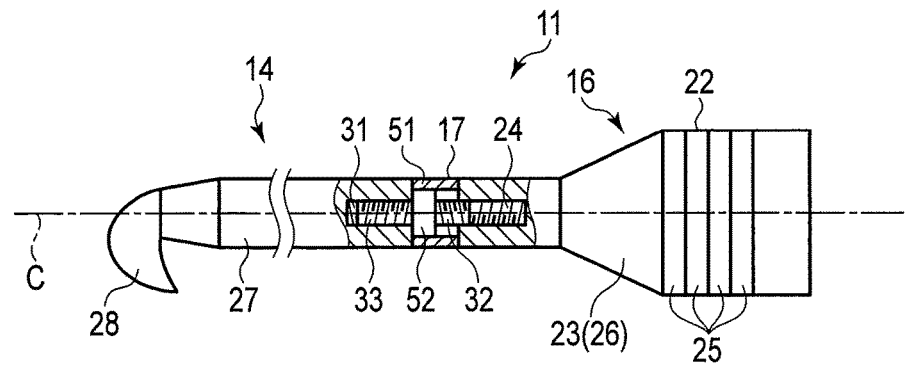
FIG. 14 is a side view showing a state in which the connecting unit of the ultrasonic treatment device shown in FIG. 13 has been fastened to a first screw portion and a second screw portion.

Functions of the ultrasonic treatment device 11 of the embodiment will be described with reference to FIG. 11, FIG. 13 and FIG. 14. In the state where the ultrasonic treatment device 11 of the embodiment has been assembled, the tip (hook-shaped projected end) of the treatment unit 28 projects toward the upper side of the figure, for example, as shown in FIG. 11.

When performing surgery, to change the position of the tip of the treatment unit 28, the doctor rotates the connecting unit 17 clockwise (in a second direction) as viewed from the proximal direction C2 around the longitudinal axis C with a finger or a device. Accordingly, the engagement between the first screw portion 24 and the first engagement portion 32 is released and the engagement between the second screw portion 31 and the second engagement portion 33 is released. Then, as shown in FIG. 13, the treatment unit 28 is arranged at a desired position (for example, the position where the tip of the treatment unit 28 projects toward the bottom side of the figure) and the connecting unit 17 is made to face the first screw portion 24. In this state, the probe 14 is held by one hand (for example, the left hand) to maintain the angle of the probe 14. At the same time, while a portion near the distal end of the vibration generating unit 16 is supported by the ring finger and the little finger of the other hand (for example, the right hand), the connecting unit 17 is rotated counterclockwise (in a first direction) as viewed from the proximal direction C2 around the longitudinal axis C with the thumb and the index finger of the other hand. As a result, the second screw portion 31 on the side of the probe 14 is pulled in toward the connecting unit 17. At the same time, the first screw portion 24 on the side of the vibration generating unit 16 is also pulled in toward an inner part of the connecting unit 17. Then, when the connecting unit 17 is rotated by a predetermined angle, the spacing member 51 of the connecting unit 17 is sandwiched between the vibration generating unit 16 and the probe 14. When the spacing member 51 is sandwiched between the vibration generating unit 16 and the probe 14 and a predetermined pressure is applied, as shown in FIG. 14, ultrasonic vibrations can be transmitted from the vibration generating unit 16 to the side of the probe 14. Thus, the doctor can easily change the angle (position) of the treatment unit 28 around the axis. After changing the angular position of the treatment unit 28, the doctor can promptly restart the treatment.

In the second embodiment, each of the first screw portion 24 and the second screw portion 31 is formed of a female screw, and each of the first engagement portion 32 and the second engagement portion 33 is formed of a male screw. The configuration described above realizes the ultrasonic treatment device 11 with a simple structure, in which an angle of the probe 14 can be freely changed.

Furthermore, the connecting unit 17 comprises the annular spacing member 51 sandwiched between the vibration generating unit 16 and the probe 14 in a state where the vibration generating unit 16 and the probe 14 are connected, and the fastening member 52 comprising the first engagement portion 32 and the second engagement portion 33, movable relative to the spacing member 51 along the longitudinal axis C, and inserted through the spacing member 51 so as to be rotatable around the longitudinal axis C together with the spacing member 51. With this configuration, the connecting unit 17, the distal end portion of the vibration generating unit 16 and the probe 14 can be the same diameter with a simple structure. Accordingly, the ultrasonic treatment device 11 can be realized, which maintains the stiffness of all of the connecting unit 17, the distal end portion of the vibration generating unit 16 and the probe 14.

Figure 15:
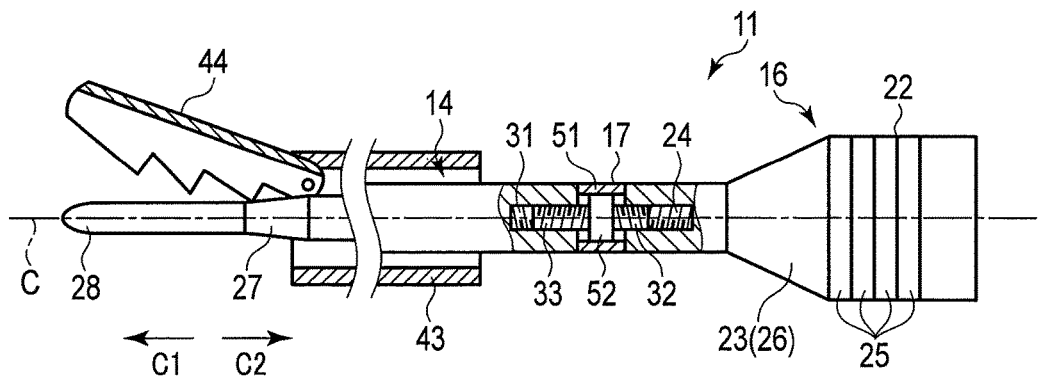
FIG. 15 is a partly cutaway schematic view of a fourth modification of the ultrasonic treatment device of the second embodiment, as viewed from a side surface.

The first modification (FIG. 7), the second modification (FIG. 8) and the third modification (FIG. 9) of the first embodiment may be adopted in the second embodiment as first, second and third modifications. A fourth modification of the second embodiment is shown in FIG. 15. As well as the fourth modification of the first embodiment, the fourth modification of the second embodiment may adopt a structure comprising a cylindrical probe 14 and a grasping member 44 for grasping living tissue. The fourth modification of the second embodiment is different from the second embodiment in the probe unit 14 and the grasping member 44; the other parts are the same as those of the second embodiment.

Subsequently, an ultrasonic treatment device 11 of a fifth modification of the second embodiment will be described with reference to FIG. 16 to FIG. 19. The fifth modification is different from the fourth modification of the second embodiment in having a knob 61 to rotate the connecting unit 17; the other parts are the same as those of the fourth modification of the second embodiment.

The hand piece 12 of the ultrasonic treatment device 11 comprises the knob 61. The knob 61 is attached to a circumference of the spacing member 51 of the connecting unit 17. The knob 61 is formed of, for example, an alloy such as duralumin, or another metal or alloy, and shaped like a letter "P". The knob 61 is not limited to the above material, but may be formed of, for example, resin material or fiber-reinforced resin material.

The knob 61 comprises an annular portion 62 to be positioned around the connecting unit 17, a finger hook portion 63 projecting from the annular portion 62, a spring portion 66 connecting the annular portion 62 and the finger hook portion 63 and providing flexibility, a claw portion 64 projecting from the finger hook portion 63 toward the annular portion 62, and a clutch 65 projecting from a side of the annular portion 62 toward the finger hook portion 63 (the claw portion 64). The annular portion 62, the finger hook portion 63, the spring portion 66, the claw portion 64 and the clutch 65 are formed integrally.

Figure 17:
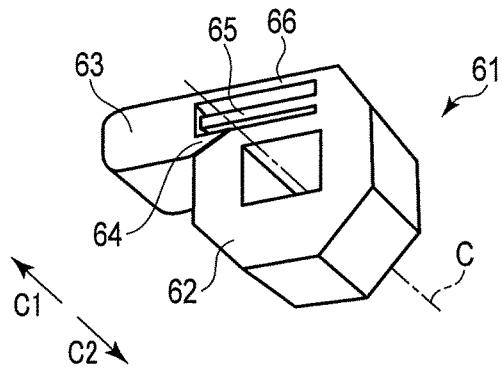
FIG. 17 is a perspective view showing a state before rotating a knob of the ultrasonic treatment device shown in FIG. 16.
Figure 18:
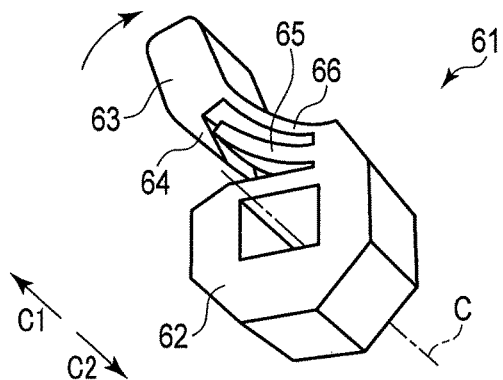
FIG. 18 is a perspective view showing a state of the knob of the ultrasonic treatment device shown in FIG. 17, in which a clutch is engaged with a claw portion while the knob is rotating.
Figure 19:
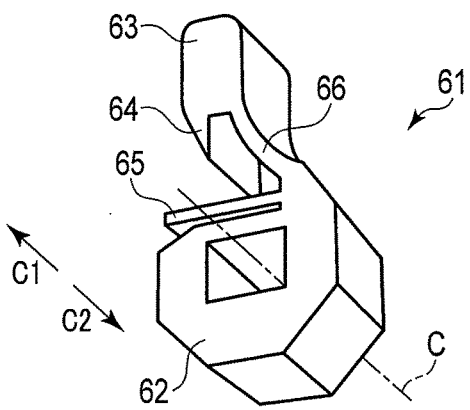
FIG. 19 is a perspective view showing a state of the knob of the ultrasonic treatment device shown in FIG. 17, in which the clutch is disengaged from the claw portion while the knob is rotating.

Subsequently, functions of the knob 61 will be described with reference to FIG. 17 to FIG. 19. When the position (angle) of the probe 14 about the axis is to be changed, as in the second embodiment described above, the doctor rotates the connecting unit clockwise (in the second direction) as viewed from the proximal direction C2 around the longitudinal axis C with the finger hook portion 63 of the knob 61. Accordingly, the engagement between the first screw portion 24 and the first engagement portion 32 is released and the engagement between the second screw portion 31 and the second engagement portion 33 is released. At this time, torque applied to the finger hook portion 63 by the doctor is entirely transferred to the side of the annular portion 62 via the claw portion 64 that is in contact with the annular portion 62, as shown in FIG. 17.

Figure 16:
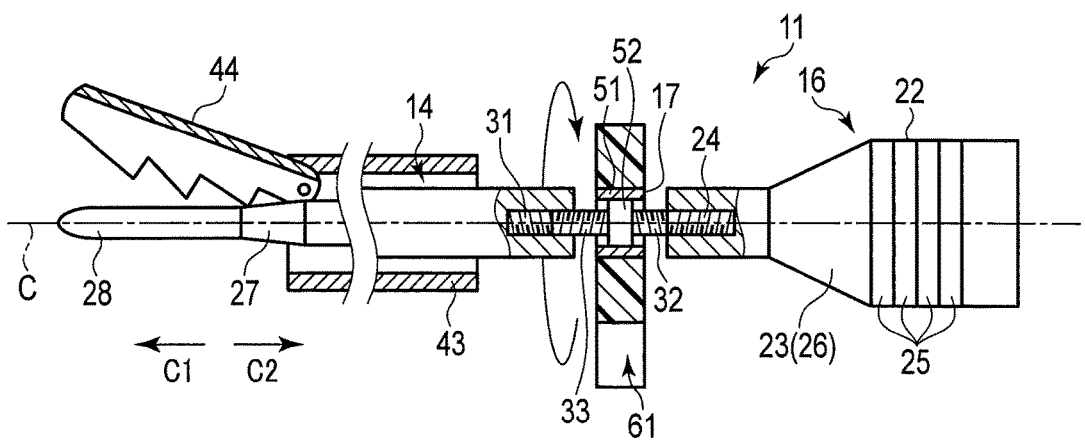
FIG. 16 is a partly cutaway schematic view of a fifth modification of the ultrasonic treatment device of the second embodiment, as viewed from a side surface.

Furthermore, as shown in FIG. 16, the probe 14 and the grasping member 44 are placed at a desired position (angle) around the axis, and the connecting unit 17 is made to face the first screw portion 24. In this state, the probe 14 and the sheath 43 are held by one hand (for example, the left hand) to maintain the angle of the probe 14. At the same time, while a portion near the distal end of the vibration generating unit 16 is supported by the ring finger and the little finger of the other hand (for example, the right hand), the knob 61 is rotated counterclockwise (in the first direction) as viewed from the proximal direction C2 around the longitudinal axis C with the finger hook portion 63 held by the thumb and the index finger of the other hand. As a result, the second screw portion 31 on the side of the probe 14 is pulled in toward the side of the connecting unit 17. At the same time, the first screw portion 24 on the side of the vibration generating unit 16 is also pulled in toward an inner part of the connecting unit 17. Then, when the connecting unit 17 is rotated by a predetermined angle with the knob 61, the spacing member 51 of the connecting unit 17 is sandwiched between the vibration generating unit 16 and the probe 14. At this time, when the knob 61 rotates counterclockwise around the longitudinal axis C as viewed from the proximal direction C2, the knob 61 is deformed from the state shown in FIG. 17 to a state shown in FIG. 18. In the state shown in FIG. 18, since the clutch 65 engages with the claw portion 64, a certain amount of torque is applied to the connecting unit 17 even while the knob 61 is rotating. When the torque to fasten the first engagement portion 32 to the first screw portion 24 and the torque to fasten the second engagement portion 33 to the second screw portion 31 reach a predetermined value, the engagement of the clutch 65 to the claw portion 64 is released and the knob 61 is brought to a state shown in FIG. 19. As a result, the connecting unit 17 is brought to a state in which the torque cannot be applied any further, and the connecting unit 17 is fastened to the vibration generating unit 16 and the probe 14 with torque of the predetermined value.

While the connecting unit 17 is fastened by the knob 61, when the spacing member 51 is sandwiched between the vibration generating unit 16 and the probe 14 and a predetermined pressure is applied (see FIG. 15 etc.), ultrasonic vibrations can be transmitted from the vibration generating unit 16 to the side of the probe 14. After changing the angle of the treatment unit 28, the doctor can promptly restart the treatment.

The modification comprises the knob 61, which is provided in the connecting unit 17 and fastens the connecting unit 17 to the vibration generating unit 16 and the probe 14 with a certain amount of torque. With this configuration, the connecting unit 17 can be fastened to the vibration generating unit 16 and the probe 14 with a certain amount of torque. Therefore, a device, such as a torque wrench to fasten the connecting unit 17, need not be used, which can obviate the need for cleanness management of a torque wrench. Furthermore, since the connecting unit 17 cannot be fastened with torque exceeding the predetermined value, a malfunction such as damage of the connecting unit 17 can be prevented.

In this modification, the knob 61 directly engages with the connecting unit 17. However, the knob 61 may be fixed to the connecting unit 17 via a fixing member, such as a clip or a pin. If the probe 14 is a single-use product, at least one of the connecting unit 17 and the knob 61 may be partly or entirely formed of a material which is not resistant to sterilization, such as autoclaving (for example, a resin material having a low fusing or softening point). Thus, unintended reuse of the probe 14 can be prevented.

The description of this embodiment relates to a case in which the knob 61 is combined with the connecting unit 17 of the second embodiment. However, the knob 61 may also be combined with the connecting unit 16 of the first embodiment in the same manner.

Third Embodiment

An ultrasonic treatment device 11 of a third embodiment will be described with reference to FIG. 20 and FIG. 21. The ultrasonic treatment device 11 of the third embodiment differs from the first embodiment in that it comprises a chuck 70 instead of the connecting unit 71, a coupling portion 71 in the vibration generating unit 16, and a screw portion 72 to secure the chuck 70 to a proximal end portion of the probe 14. The other parts are the same as those of the first embodiment, therefore, mainly those portions different from the first embodiment will be explained. Portions that are the same as the first embodiment will not be explained or illustrated in the drawings.

The chuck 70 includes a butting member 73 which is directly brought into contact with the coupling portion 71 of the vibration generating unit 16, a base member 74 supporting the butting member 73 and secured to the screw portion 72 of the probe 14 (the probe main body 27), and an annular operating member 75 which is brought into contact with the butting member 73 to operate the butting member 73. Each of the butting member 73, the base member 74 and the operating member 75 is formed of, for example, a metal material for a mechanical structure, which preferably has a small specific gravity and minimally attenuates ultrasonic waves (e.g., a titanium alloy or an aluminum alloy).

The butting member 73 is formed integrally with the base member 74. The butting member 73 includes a plurality of (for example, four) finger-like portions 76 projecting from the base member 74 toward the distal direction C2 along the longitudinal axis C, and a catching portion 79 provided at a base of the finger-like portions 76. A slit 77 is provided between adjacent finger-like portions 76. The finger-like portions 76 as a whole form a circular shape, and are configured to receive the coupling portion 71 on the side of the vibration generating unit 16 in an opening 78 inside the circular shape. As shown in FIG. 21, the finger-like portions 76 are movable (deformable) in directions crossing the longitudinal axis C between a contact position S1 in contact with a circumferential surface of the coupling portion 71 and a separate position S2 separated from the circumferential surface of the coupling portion 71.

The vibration generating unit 16 includes the coupling portion 71 on the side of the distal direction C1. The coupling portion 71 extends like a rod from the main body of the vibration generating unit 16 in the distal direction C1 along the longitudinal axis C. The coupling portion 71 has a so-called inverse tapered shape, whose diameter gradually increases toward the distal end.

As shown in FIG. 20, the operating member 75 has a so-called hat shape having a through hole 75A in a central portion along the longitudinal axis C. The finger-like portions 76 of the butting member 73 can be inserted in the through hole 75A. As shown in FIG. 21, the operating member 75 has a projection 81 annularly projecting from the inner surface in the through hole 75A toward the center. The operating member 75 is slidable relative to the butting member 73 along the longitudinal axis C. The operating member 75 is configured to move between a first position P1 in contact with the butting member 73 to force the butting member 73 to be placed in the contact position S1 and a second position P2 separate from the butting member 73 toward the base member 74 to place the butting member 73 in the separate position S2. When the operating member 75 is in the first position P1, the butting member 73 securely holds the coupling portion 71, so that the probe 14 is fixed to the vibration generating unit 16, that is, in a lock state. Simultaneously at this time, since the circumferential surface of the end portion 71 has the inverse tapered shape, the portion is pulled in the direction C1 by the finger-like portions 76 which are closed. Thus, since the end portion 71 and the probe 14 butt against each other and are fixed with a predetermined pressure exerted, the ultrasonic vibrations are also smoothly transmitted from the side of the vibration generating unit 16 to the side of the probe 14. Furthermore, when the operating member 75 is in the first position P1, the projection 81 is fit within the catching portion 79. Therefore, the operating member 75 in the first position P1 is restricted from free movement. Accordingly, the probe 14 is prevented from being detached by unintentional movement of the operating member 75 while the ultrasonic treatment device 11 is being used.

The projection 81 may be omitted, if the operating member 75 is restricted from moving in the direction C2 due to a dimensional relationship among the outer circumference of the end portion 71, the finger-like portions 76 and the operating member 75, such that they are in a press-fit condition when the operating member 75 is in the first position P1.

Functions of the ultrasonic treatment device 11 of this embodiment will be described. When performing surgery, to change an angular position of the tip of the treatment unit 28 about the axis, the doctor moves the operating member of the chuck 70 from the first position P1 to the second position P2, as shown in FIG. 21, thereby releasing the lock state of the coupling portion 71 by the butting member 73. The treatment unit 28 is arranged in a desired position (angle), and the coupling portion 71 is inserted in the butting member 73 (finger-like portions 76) of the chuck 70. In this state, the probe 14 is held by one hand (for example, the left hand) to maintain the angle of the probe 14. At the same time, while a portion near the distal end of the vibration generating unit 16 is supported by the ring finger and the little finger of the other hand (for example, the right hand), the operating member 75 is moved from the second position P2 to the first position P1 with the thumb and the index finger of the other hand. As a result, the coupling portion 71 on the side of the vibration generating unit 16 is pulled toward the side of the probe 14. When the end face of the coupling portion 71 butts against the end face of the screw portion 72 of the probe 14, and a predetermined pressure is applied, as shown in FIG. 21, ultrasonic vibrations can be transmitted from the vibration generating unit 16 to the side of the probe 14. Thus, the doctor can easily change the angle (position) of the treatment unit 28. After changing the angle of the treatment unit 28, the doctor can promptly restart the treatment.

The ultrasonic treatment device 11 of this embodiment comprises: the vibration generating unit 16 which includes the coupling portion 71 and generates ultrasonic vibrations; the probe 14 including the probe main body 27 which extends along the longitudinal axis C and to which the ultrasonic vibrations generated by the vibration generating unit 16 are transmitted and the treatment unit 28 provided at a distal end portion of the probe main body 27; and the chuck 70 secured to the probe main body 27 and configured to grasp the coupling portion 71 to transmit the ultrasonic vibrations to the probe and release the coupling portion 71.

The configuration described above realizes the ultrasonic treatment device 11 with a simple structure, in which an angle of the probe 14 can be freely changed. Furthermore, since the connecting unit 17 connects the probe 14 and the vibration generating unit 16 so as to transmit ultrasonic vibrations to the side of the probe 14, the loss of ultrasonic vibrations at a boundary position between the vibration generating unit 16 and the probe 14 can be suppressed to a minimum. Furthermore, since the chuck 70 is secured to the probe main body 27, a complicated structure, such as the chuck 70, can be arranged on the side of the probe 14 which is a single-use product. With this modification, when the vibration generating unit 16 to be repeatedly used is reprocessed, the work burden can be reduced and a reprocess defect will be unlikely to occur.

The chuck 70 includes the butting member 73 which is movable in directions crossing the longitudinal axis C between the contact position S1 in contact with the circumferential surface of the coupling portion 71 and the separate position S2 separated from the circumferential surface of the coupling portion 71; and the operating member 75 movable along the longitudinal axis C between the first position P1 in contact with the butting member 73 from an outer side of the butting member 73 to force the butting member 73 to be placed in the contact position S1 and the second position P2 separate from the butting member 73 to place the butting member 73 in the separate position S2.

With this configuration, the probe 14 can be attached to and detached from a simple structure including the butting member 73 and the operating member 75 with a single motion.

Fourth Embodiment

An ultrasonic treatment device 11 of a fourth embodiment will be described with reference to FIG. 22 to FIG. 25. The ultrasonic treatment device 11 of the fourth embodiment differs from the first embodiment in that a vibration generating unit 16 and a probe 14 each have a hole inside. The other parts are the same as those of the first embodiment, therefore, mainly those portions different from the first embodiment will be explained. Portions that are the same as the first embodiment will not be explained or illustrated in the drawings.

As shown in FIG. 22 and FIG. 23, the vibration generating unit 16 comprises an ultrasonic vibrator 22, a horn member 23, a first screw portion 24 and a first hole 82 extending therethrough. The first hole 82 extends over the entire length of the vibration generating unit 16 from the proximal direction C2 to the distal direction C1 along the longitudinal axis C.

The probe 14 comprises a probe main body 27 extended along the longitudinal axis C, a second screw portion 31 provided on the probe main body 27 to face the first screw portion 24, a treatment unit 28 provided on the side of the distal direction C1 of the probe main body 27, and a second hole 83 extending therethrough. The second hole 83 extends over the entire length of the probe 14 from the proximal direction C2 to the distal direction C1 along the longitudinal axis C. The treatment unit 28 of this embodiment is rod-shaped. The first screw portion 24, the second screw portion 31, and the connecting unit 17 are the same in configuration as those of the first embodiment.

This embodiment is configured to perform suctioning from the treatment unit 28 through the first hole 82 and the second hole 83 by a suction pump connected to the holes. Similarly, water can be supplied to the treatment unit 28 through the first hole 82 and the second hole 83 by a water pump connected to the holes.

Functions of the ultrasonic treatment device 11 of the embodiment will be described with reference to FIG. 22, FIG. 24 and FIG. 25. In the state where the ultrasonic treatment device 11 of the embodiment has been assembled, the tip of the treatment unit 28 projects toward the bottom side of the figure, for example, as shown in FIG. 22.

When performing surgery, to change the position of the tip of the treatment unit 28, the doctor rotates the probe 14 and the connecting unit 17 clockwise (in a second direction) as viewed from the proximal direction C2 around the longitudinal axis C, thereby releasing the engagement between the first screw portion 24 and the first engagement portion 32. Then, as shown in FIG. 24, the treatment unit 28 is arranged at a desired position (for example, the position where the tip of the treatment unit 28 projects toward the upper side of the figure) and the connecting unit 17 is made to face the first screw portion 24. In this state, the probe 14 is held by one hand (for example, the left hand) to maintain the angle of the probe 14. At the same time, while a portion near the distal end of the vibration generating unit 16 is supported by the ring finger and the little finger of the other hand (for example, the right hand), the connecting unit 17 is rotated counterclockwise (in a first direction) as viewed from the proximal direction C2 around the longitudinal axis C with the thumb and the index finger of the other hand. As a result, the second screw portion 31 on the side of the probe 14 is pulled in toward an inner part of the connecting unit 17 (toward the clearance portion 34). At the same time, the first screw portion 24 on the side of the vibration generating unit 16 is also pulled in toward an inner part of the connecting unit 17 (toward the clearance portion 34). When the connecting unit 17 is rotated by a predetermined angle, the end face of the first screw portion 24 is made to butt against the end face of the second screw portion 31. When the end face of the first screw portion 24 butts against the end face of the second screw portion 31 and a predetermined pressure is applied, ultrasonic vibrations can be transmitted from the vibration generating unit 16 to the side of the probe 14. Thus, the doctor can easily change the angle (position) of the treatment unit 28. After changing the angle of the treatment unit 28, the doctor can promptly restart the treatment.

The embodiment described above realizes the ultrasonic treatment device 11 with a simple structure, in which an angle of the probe 14 can be freely changed. Furthermore, since the connecting unit 17 connects the probe 14 and the vibration generating unit 16 so as to transmit ultrasonic vibrations to the side of the probe 14, the loss of ultrasonic vibrations at a boundary position between the vibration generating unit 16 and the probe 14 can be suppressed to a minimum. Furthermore, since the first hole 82 and the second hole 83 are incorporated in the probe 14 and the vibration generating unit 16, a malfunction, such as twisting of a pipe for suctioning or water supply, can be prevented when the position (angle) of the treatment unit 28 is being changed.

Fifth Embodiment

An ultrasonic treatment device 11 of a fifth embodiment will be described with reference to FIG. 26 and FIG. 27. The ultrasonic treatment device 11 of the fifth embodiment differs from the first embodiment in that a probe 14 is divided into a first portion 14A and a second portion 14B, that the probe 14 includes a connecting unit 17, and that the connecting unit 17 connects the first portion 14A and the second portion 14B. The other parts are the same as those of the first embodiment, therefore, mainly those portions different from the first embodiment will be explained. Portions that are the same as the first embodiment will not be explained or illustrated in the drawings.

As shown in FIG. 27, a vibration generating unit 16 comprises an ultrasonic vibrator 22, a horn member 23, and a first connecting end portion 84. The ultrasonic vibrator 22 and the horn member 23 are the same in configuration as those of the first embodiment. The first connecting end portion 84 is provided on a side of the distal direction C1 along the longitudinal axis C. The first connecting end portion 84 comprises a female screw, and corresponds to a second connecting end portion 85 comprising a male screw.

The probe 14 is formed of, for example, a biocompatible metal material (e.g., a titanium alloy). As shown in FIG. 27, the probe 14 comprises the first portion 14A located on a side of the vibration generating unit 16 and extending along the longitudinal axis C; a first screw portion 24 provided on a side of a distal direction of the first portion 14A; the second connecting end portion 85 provided on a side of a proximal direction C2 of the first portion 14A; the second portion 14B closer to an end in the distal direction C1 than the first portion 14A and extending along the longitudinal axis C; a second screw portion 31 provided on a side of the proximal direction C2 of the second portion 14B to face the first screw portion 24; a treatment unit 28 provided on a side of the distal direction C1 of the second portion 14B; and the connecting unit 17 that connects the first portion 14A and the second portion 14B.

The first portion 14A and the second portion 14B each have a rod shape extending along the longitudinal axis C. The treatment unit 28 has, for example, a blade extending in a direction crossing the longitudinal axis C; it has a hook-like shape. The first screw portion 24, the second screw portion 31, and the connecting unit 17 are the same in configuration as those of the first embodiment.

The second connecting end portion 85 comprises a male screw, more specifically, a right-handed screw. In this embodiment, the second connecting end portion 85 is fastened to the first connecting end portion 84, so that the probe 14 can be secured to the vibration generating unit 16.

Functions of the ultrasonic treatment device 11 of this embodiment are principally the same as those of the first embodiment. Thus, the doctor can easily change the angle (position) of the treatment unit 28 by operating the connecting unit 17. Furthermore, in this embodiment, the probe 14 is rotated clockwise around the longitudinal axis C as viewed from the proximal direction C2, thereby releasing the engagement between the first connecting end portion 84 and the second connecting end portion 85. Thus, the probe 14 can be removed from the vibration generating unit 16, Moreover, as shown in FIG. 26, the probe 14 is rotated counterclockwise around the longitudinal axis C as viewed from the proximal direction C2, thereby fastening the second connecting end portion 85 to the first connecting end portion 84. Thus, the probe 14 can be secured to the vibration generating unit 16.

The length of the probe 14 and the vibration generating unit 16 (the horn member 23) along the longitudinal axis C, which most influences the drive frequency, has a constant value, since the end face of the first screw portion 24 butts against the end face of the second screw portion 31.

According to the fifth embodiment, the probe 14 comprises: the first portion 14A which extends along the longitudinal axis C and has the first screw portion 24, and to which ultrasonic vibrations are transmitted; the second portion 14B which extends along the longitudinal axis C; the second screw portion 31 provided in the second portion 14B to face the first screw portion 24 and having a spiral in an opposite direction to that of the first screw portion 24; the treatment unit 28 provided on a distal end portion of the second portion 14B; and the connecting unit 17 including the first engagement portion 32 which engages with the first screw portion 24 and the second engagement portion 33 which engages with the second screw portion 31, wherein the connecting unit 17 connects the first portion 14A and the second portion 14B so as to transmit ultrasonic vibrations to the side of the second portion 14B by rotation relative to the first portion 14A and the second portion 14B in a first direction around the longitudinal axis C, and disconnects the first portion 14A and the second portion 14B from each other by rotation in a second direction opposite to the first direction.

This configuration realizes a simple structure, in which the position (angle) of the second portion 14B relative to the first portion 14A can be adjusted in the so-called probe 14. Furthermore, since the connecting unit 17 connects the probe 14 and the vibration generating unit 16 so as to transmit ultrasonic vibrations to the side of the probe 14, the loss of ultrasonic vibrations at a boundary position between the vibration generating unit 16 and the probe 14 can be suppressed to a minimum.

The present invention is not limited to the embodiments described above, and various modifications may be made without departing from the gist of the invention. Furthermore, it is naturally possible that the ultrasonic treatment devices 11 of some of the embodiments be combined to constitute one ultrasonic treatment device.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

REFERENCE SIGNS LIST

11 . . . ultrasonic treatment device, 14 . . . probe, 14A . . . first portion, 14B . . . second portion, C . . . longitudinal axis, 16 . . . vibration generating unit, 17 . . . connecting unit, 24 . . . first screw portion, C1 . . . distal direction, C2 . . . proximal direction, 27 . . . probe main body, 28 . . . treatment unit, 31 . . . second screw portion, 32 . . . first engagement portion, 33 . . . second engagement portion, 35 . . . recess, 36 . . . fitting portion, 37 . . . concave portion, 41 . . . first projection, 42 . . . second projection, 51 . . . spacing member, 52 . . . fastening member, 61 . . . knob, 70 . . . chuck, 71 . . . coupling portion, 73 . . . butting member, 75 . . . operating member, S1 . . . contact position, S2 . . . separate position, P1 . . . first position, P2 . . . second position.

What is claimed is:

1. An ultrasonic treatment device comprising:
a vibration generating unit including a first screw portion, the vibration generating unit generating ultrasonic vibrations;
a probe including:
a probe main body that extends along a longitudinal axis and to which the ultrasonic vibrations generated by the vibration generating unit are transmitted,
a second screw portion that is provided at the probe main body such that the second screw portion faces the first screw portion, the second screw portion having a spiral in an opposite direction to that of the first screw portion, and
a treatment unit at a distal end portion of the probe main body;
a connecting unit including:
a first engagement portion in which a female screw corresponding to the first screw portion is formed, and
a second engagement portion in which a female screw corresponding to the second screw portion is formed; and
a knob attached to the connecting unit, the knob fastening the connecting unit to the vibration generating unit and the probe with specific torque,
wherein:
the connecting unit is configured to connect the probe with the vibration generating unit to transmit the ultrasonic vibrations to the probe by rotation relative to the vibration generating unit and the treatment unit in a first direction around the longitudinal axis by engaging the first screw portion with the female screw of the first engagement portion and pulling the first screw portion, and by engaging the second screw portion with the female screw of the second engagement portion and pulling the second screw portions, and disconnecting the probe and the vibration generating unit from each other by rotation in a second direction opposite to the first direction, and
the connecting unit is disposed on the ultrasonic treatment device at a position apart from a node of the ultrasonic vibrations.

2. An ultrasonic treatment device comprising:
a vibration generating unit including a first screw portion, the vibration generating unit generating ultrasonic vibrations;
a probe including:
a probe main body that extends along a longitudinal axis and to which the ultrasonic vibrations generated by the vibration generating unit are transmitted,
a second screw portion that is provided at the probe main body such that the second screw portion faces the first screw portion, the second screw portion having a spiral in an opposite direction to that of the first screw portion, and
a treatment unit at a distal end portion of the probe main body; and
a connecting unit including:
a first engagement portion in which a female screw corresponding to the first screw portion is formed, and
a second engagement portion in which a female screw corresponding to the second screw portion is formed,
wherein:
the connecting unit is configured to connect the probe with the vibration generating unit to transmit the ultrasonic vibrations to the probe by rotation relative to the vibration generating unit and the treatment unit in a first direction around the longitudinal axis by engaging the first screw portion with the female screw of the first engagement portion and pulling the first screw portion, and by engaging the second screw portion with the female screw of the second engagement portion and pulling the second screw portions, and disconnecting the probe and the vibration generating unit from each other by rotation in a second direction opposite to the first direction,
the connecting unit is disposed on the ultrasonic treatment device at a position apart from a node of the ultrasonic vibrations,
an end face of the first screw portion is configured to be brought into contact with an end face of the second screw portion in a state where the vibration generating unit and the probe are connected by the connecting unit, and
the ultrasonic treatment device further comprises at least one of (i) a first projection projecting from the end face of the first screw portion and configured to be brought into contact with the end face of the second screw portion and (ii) a second projection projecting from the end face of the second screw portion and configured to be brought into contact with the end face of the first screw portion.

3. An ultrasonic treatment device comprising:
a vibration generating unit including a first screw portion, the vibration generating unit generating ultrasonic vibrations;
a probe including:
a probe main body that extends along a longitudinal axis and to which the ultrasonic vibrations generated by the vibration generating unit are transmitted,
a second screw portion that is provided at the probe main body such that the second screw portion faces the first screw portion, the second screw portion having a spiral in an opposite direction to that of the first screw portion, and
a treatment unit at a distal end portion of the probe main body; and
a connecting unit including:
a first engagement portion in which a female screw corresponding to the first screw portion is formed,
a second engagement portion in which a female screw corresponding to the second screw portion is formed,
an annular spacing member sandwiched between the vibration generating unit and the probe in a state where the vibration generating unit and the probe are connected, and
a fastening member that comprises the first engagement portion and the second engagement portion, the fastening member being movable relative to the spacing member along the longitudinal axis and being configured to be inserted through the spacing member and rotatable around the longitudinal axis together with the spacing member,
wherein:
the connecting unit is configured to connect the probe with the vibration generating unit to transmit the ultrasonic vibrations to the probe by rotation relative to the vibration generating unit and the treatment unit in a first direction around the longitudinal axis by engaging the first screw portion with the female screw of the first engagement portion and pulling the first screw portion, and by engaging the second screw portion with the female screw of the second engagement portion and pulling the second screw portions, and disconnecting the probe and the vibration generating unit from each other by rotation in a second direction opposite to the first direction, and
the connecting unit is disposed on the ultrasonic treatment device at a position apart from a node of the ultrasonic vibrations.

\* \* \* \* \*